United States Patent
Wu et al.

(10) Patent No.: US 7,077,809 B2
(45) Date of Patent: Jul. 18, 2006

(54) SYSTEM FOR MEASURING AND ANALYZING VASODILATATION INDEX

(75) Inventors: Hsien-Tsai Wu, Tainan (TW); Chih-Kai Chi, Tainan (TW); Yung-Kang Chen, Kaohsiung (TW)

(73) Assignee: Hsien-Tsao WU, Tainan (TW)

( * ) Notice: Subject to any disclaimer, the term of this patent is extended or adjusted under 35 U.S.C. 154(b) by 0 days.

(21) Appl. No.: 10/840,648

(22) Filed: May 7, 2004

(65) Prior Publication Data

US 2004/0254485 A1    Dec. 16, 2004

(30) Foreign Application Priority Data

May 21, 2003 (TW) .............................. 92113734 A (51) Int. Cl.
    *A61B 5/02* (2006.01)
(52) U.S. Cl. ........................................ 600/490; 600/500
(58) Field of Classification Search ........ 600/500–504, 600/507, 322–324, 335, 336, 490, 492–497
    See application file for complete search history.

(56) References Cited

U.S. PATENT DOCUMENTS

| | | | |
|---|---|---|---|
| 5,485,838 A * | 1/1996 | Ukawa et al. .............. 600/330 |
| 5,830,149 A * | 11/1998 | Oka et al. ................... 600/500 |
| 6,241,680 B1 * | 6/2001 | Miwa .......................... 600/494 |
| 6,371,922 B1 * | 4/2002 | Baumann et al. ........... 600/485 |
| 6,599,251 B1 * | 7/2003 | Chen et al. ................. 600/485 |
| 6,719,704 B1 * | 4/2004 | Narimatsu et al. .......... 600/500 |
| 6,939,304 B1 * | 9/2005 | Schnall et al. .............. 600/481 |

* cited by examiner

*Primary Examiner*—Max F. Hindenburg
*Assistant Examiner*—Navin Natnithithadha
(74) *Attorney, Agent, or Firm*—Banner & Witcoff, Ltd.

(57) ABSTRACT

In a vasodilatation index measuring and analyzing system, a measuring unit includes a measuring device for measuring standard and comparative pulses of a digit of a subject in relaxed and comparative states, respectively. An external pressure is applied to a limb part of the subject to occlude blood flow to the digit following measurement of the standard pulse. The comparative pulse is measured upon release of the external pressure. A pre-processing unit is coupled to the measuring unit for filtering noise from and digitizing the standard and comparative pulses obtained by the measuring device. An analyzing unit is coupled to the pre-processing unit for calculating standard and comparative pulse areas of at least one cycle of the standard and comparative pulses processed by the pre-processing unit, respectively, and for subsequently calculating a pre-defined index related to a difference between the standard and comparative pulse areas.

15 Claims, 7 Drawing Sheets

SYSTEM FOR MEASURING AND ANALYZING VASODILATATION INDEX

CROSS-REFERENCE TO RELATED APPLICATION

This application claims priority of Taiwanese Application No. 092113734, filed on May 21, 2003.

BACKGROUND OF THE INVENTION

1. Field of the Invention

This invention relates to a measuring and analyzing system, more particularly to a non-invasive system for measuring and analyzing the vasodilatation index to determine the endothelial function of blood vessels so as to serve as a reference index for coronary atherosclerosis.

2. Description of the Related Art

Cardiovascular diseases are still ranked among the top ten killers in Taiwan. Atherosclerosis and coronary arterial diseases often lead to myocardiac infarcts and heart failure, which are the major causes of death. Atherosclerosis is chiefly characterized by fat accumulation in parts of the vascular walls, and the fats are built up in the cells or in interstitial cells in the form of cholesterol or labile cholesterol. It is known that recurring impairment of endothelial cells and increased adipose infiltration are critical processes in the formation of atherosclerosis.

Endothelial cells are a layer of cells that adhere to the inside walls of arteries. These cells regulate their functions through nitric oxide (NO), a gaseous neurotransmitter responsible for signal transmission in living organisms. Nitric oxide not only is the most critical and essential signal transmitting gaseous substance in the cardiovascular system, it also has other functions. After generation by the innermost cells (endothelial cells) of the arteries, nitric oxide is quickly diffused to the smooth muscle cells under the blood vessels to inhibit contraction of vascular muscle cells to thereby result in arterial dilation. Thus, nitric oxide can be said to be a blood flow-mediated vasodilating substance capable of controlling distribution of blood and blood pressure in the blood vessels.

Endothelial cell dysfunction is the major initial step of atherosclerosis. Atherosclerosis risk factors, which include diabetes, hypertension, smoking, etc., can cause dysfunction of endothelial cells. When the endothelial cells are impaired, atherosclerosis is likely to result due to cholesterol buildup. As such, determination of the extent of endothelial cell dilation is the initial condition in the screening of atherosclerosis. Therefore, how to measure endothelial dysfunction in human beings, particularly with a non-invasive method, is a goal scientists are striving to achieve. At present, the most commonly used non-invasive method is measuring the vasodilatation of the posterior brachial artery after ischemia by ultrasonography. However, this method has limitations in that it is highly technique-dependent and highly variable. In addition, there has been developed a method of employing digital pulse to detect vasodilatation after inhalation of a beta-adrenergic agonist so as to measure the endothelial function. Although the latter method is quite simple and convenient, it has the limitation that the subject needs to inhale a bronchial dilator prior to measurement. Thus, this invention proposes a system for analyzing the endothelial function based on a measurement of the digital pulse to serve as a reference in the determination of atherosclerosis. To this end, the definition and significance of pulses as referred to herein will be described in the succeeding paragraphs.

Figure 1:
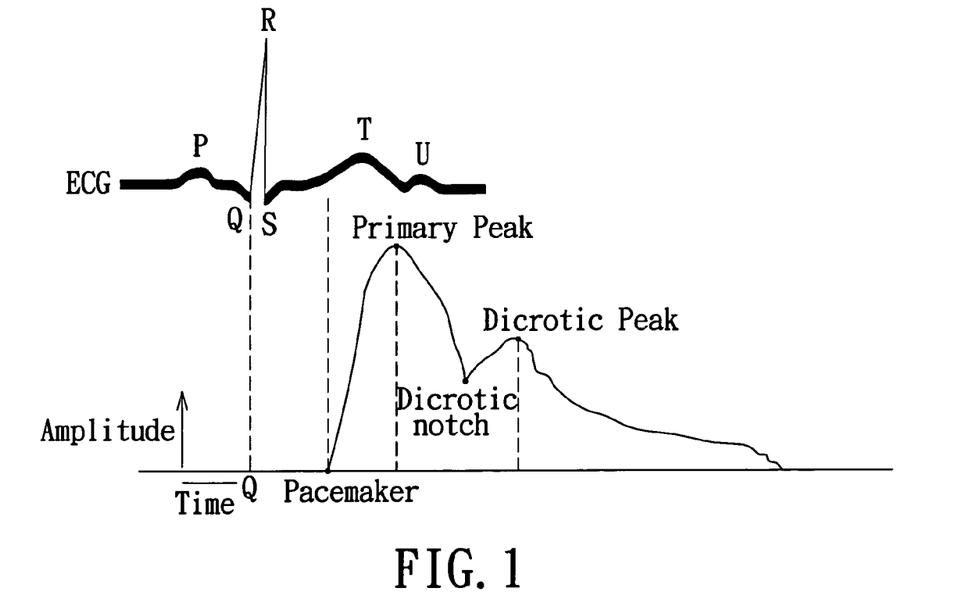
FIG. 1 is a graph illustrating the relationship between an electrocardiogram pulse output and a standard digital pulse waveform.

A cardiac cycle is divided into systolic (contraction) and diastolic (relaxation) periods, and the heart beats rhythmically and cyclically. When the heart contracts, the relatively large pressure (systolic pressure) created by the ventricles forces a large amount of blood to flow into the aorta and, at the same time, drives the blood to flow along the arteries and arterioles into the peripheral vessels. This is the rapid ejection phase. During this phase, the input of blood into the proximal aorta (proximal to the heart) exceeds the blood output so that the volume of blood in the vessels increases, thereby resulting in drastic dilation of the vascular walls. This phase corresponds to the cycle from the pacemaker to the primary peak indicated in FIG. 1. Thereafter, the ventricles enter a slow ejection phase, during which the blood input into the proximal aorta is gradually lower than the blood output so that the volume of blood in the vessels decreases, thereby resulting in a pressure drop to cause contraction of the vascular walls. Since the arteries in the human body are closed loops, at the end of the ejection phase when the blood flows to the distal ends of the vessels, the blood rebounds so that some of the blood flows back into the aortic end, thereby causing a slight increase in the volume of blood in the proximal aorta, and a relative rise in the pressure. The vascular walls at this time will also experience a transient dilation. This corresponds to the position of the dicrotic peak shown in FIG. 1. Thereafter, the vascular walls will gradually return to their normal state before contraction. Accordingly, each contraction activity of the heart results in a rise in the pressure of the blood in the proximal aorta and dilation of the vascular walls. By using a suitable light-transmissible photo sensor element, a digital volume pulse (DVP) waveform as shown in FIG. 1 can be obtained. Shown at the upper left corner of FIG. 1 is a corresponding peripheral arterial pulse waveform obtained by electrocardiogram (ECG), which exhibited a time difference with the digital volume pulse.

During the systolic phase of the ventricles, the digital volume pulse is influenced by three factors: blood ejection velocity and volume of the ventricles, the elasticity (or compliance) of the vascular wall of the proximal aorta, and the peripheral resistance of blood vessels and blood to blood flow. If the blood volume at each pulsation increases, the vascular walls of the proximal aorta can sufficiently dilate, and the dilatory waves of the vascular walls during the systolic phase can be relatively large. When the elasticity of the vascular walls of the proximal aorta declines, the extent of dilation of the vascular walls during the systolic phase is limited by the declined elasticity and is therefore relatively low. As for an increase in the resistance of the peripheral vessels, it may result in reduced flow of blood from the aorta. Thus, during the systolic phase, the tendency of the blood volume in the proximal aorta to increase speeds up, the pressure rises, and the rate and extent of vascular dilation increase. On the other hand, with a decline in the resistance of the peripheral vessels, the tendency of the blood volume in the proximal aorta to increase slows down, and the rate and extent of pressure rise and vascular dilation decrease.

In addition, during transmission, the digital volume pulse is subjected to the influence of various factors that can cause changes in the waveform of the pulse. One is the fluctuation in the attenuation constants and the transmission rates of the harmonic wave components of the pulse itself which have different frequencies. Another important factor is wave reflection. The arterial system is a highly branched vascular system. The arteries decrease in cross-sectional area and the elasticity of the arterial walls become lower as well as they are farther away from the heart. When the volume pulse is being transmitted through the arteries, in case of variations in the cross-sectional area of the arteries (such as narrowing and branching of the arteries) or changes in the characteristic of the arterial walls, the pulse will be reflected in part, thereby resulting in variations in the pulse waveform.

SUMMARY OF THE INVENTION

Therefore, the main object of the present invention is to provide a non-invasive vasodilatation index measuring and analyzing system for measuring the endothelial function of a subject so as to serve as a reference index of atherosclerosis.

Another object of this invention is to provide a vasodilatation index measuring and analyzing system which permits simultaneous multi-channel measurement to obtain measurement results for comparison so as to reduce measurement errors.

A further object of this invention is to provide a vasodilatation index measuring and analyzing system which is compact and portable and which can be a personal health-monitoring device.

Accordingly, a vasodilatation index measuring and analyzing system of this invention includes a measuring unit, a preprocessing unit, and an analyzing unit. The measuring unit includes a first measuring device for measuring a standard pulse and a comparative pulse of a first digit of a subject in a relaxed state and a comparative state, respectively, wherein an external pressure is applied to a limb part of the subject to occlude flow of blood to the first digit following measurement of the standard pulse of the first digit, the comparative pulse of the first digit being measured upon release of the external pressure. The pre-processing unit is coupled to the measuring unit for filtering noise from and digitizing the standard and comparative pulses obtained by the first measuring device. The analyzing unit is coupled to the pre-processing unit for calculating standard and comparative pulse areas of at least one cycle of the standard and comparative pulses processed by the pre-processing unit, respectively, and for subsequently calculating a pre-defined index related to a difference between the standard and comparative pulse areas.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 2:
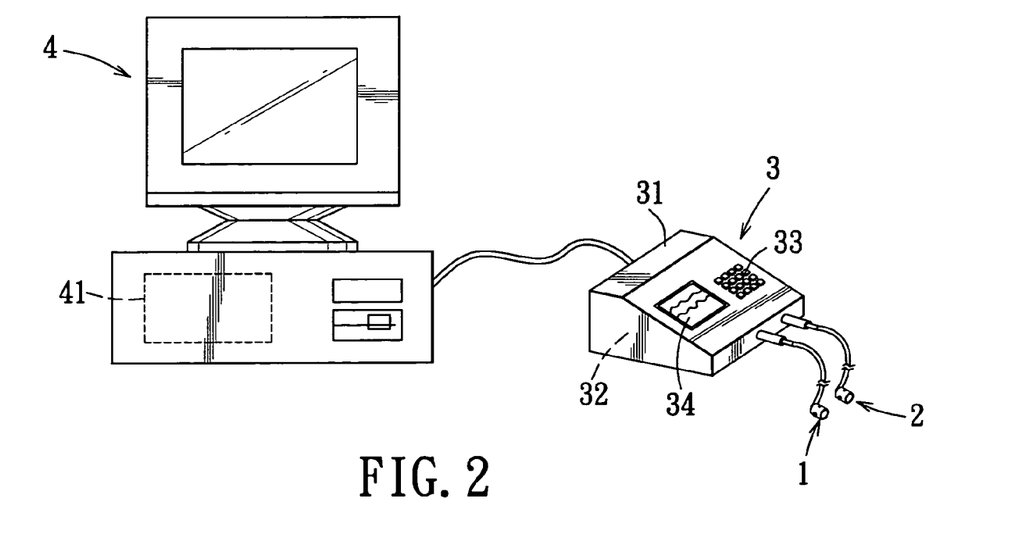
FIG. 2 is a schematic view showing the arrangement of a preferred embodiment of a vasodilatation index measuring and analyzing system according to this invention.

Referring to FIG. 2, the preferred embodiment of a vasodilatation index measuring and analyzing system according to the present invention is shown to include a measuring unit for measuring a plurality of digital pulse signals of a subject (not shown) and including a first measuring device 1 and a second measuring device 2, a pre-processing unit 3 for performing pre-processing of the digital pulse signals, and an analyzing unit 4 for calculating and analyzing the digital pulse signals data which have been digitized during pre-processing.

The first measuring device 1 and the second measuring device 2 are operable to measure simultaneously and respectively the pulses of a first digit 5 (shown in FIGS. 3 and 4) and a second digit (not shown). The first digit 5 and the second digit in this embodiment correspond respectively to a finger and a toe of the subject. In alternative embodiments, the measuring unit may be modified to include more than two measuring devices (measuring channels) for simultaneous measurement of more than two digits of the subject, and may be applied to parts of the body other than the fingers and toes, such as the wrists.

Figure 3:
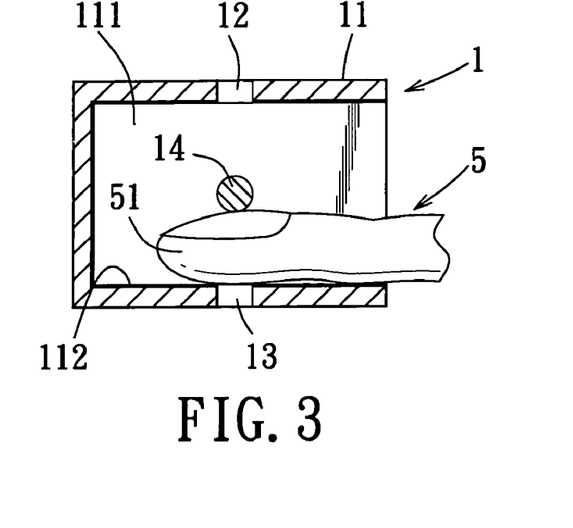
FIG. 3 is a schematic side sectional view illustrating a first measuring device of the preferred embodiment in a state of use.
Figure 4:
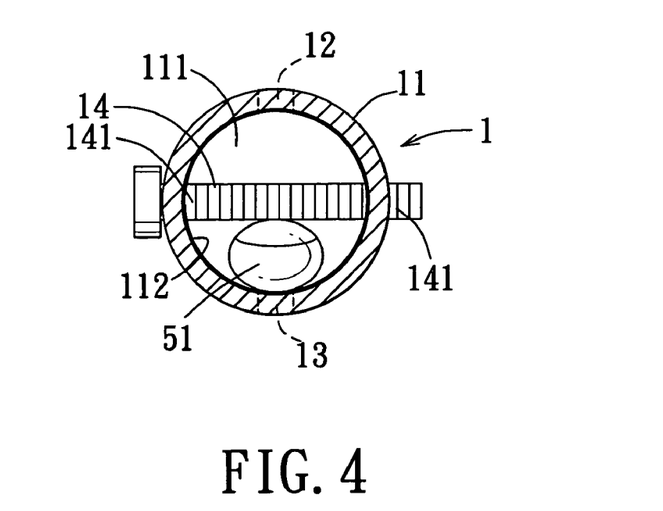
FIG. 4 is a schematic sectional view of the first measuring device shown in FIG. 3.

The first measuring device 1 of the measuring unit measures a pulse signal of the first digit 5 by emitting and receiving an optical signal through a tip portion 51 of the first digit 5. Referring to FIGS. 3 and 4, the first measuring device 1 is shown to include a ring-shaped body 11, an emitting unit 12, a receiving unit 13, and a pressing unit 14. The ring-shaped body 11 confines a chamber 111 adapted for receiving the tip portion 51, and has an inner surface applied with a black film 112 for isolating outside light interference. The emitting unit 12 and the receiving unit 13 are respectively provided at two opposite sides of the ring-shaped body 11 along a diametrical line, and are operable to respectively transmit and receive an optical signal radially in the chamber 111. In this embodiment, the optical signal is exemplified as infrared light with a wavelength of 940 nm. However, any other suitable form of light source may be adopted. The pressing unit 14 is adapted to press an upper side of the tip portion 51 (i.e., the fingernail side), and has two opposite ends 141 which extend respectively through the ring-shaped body 11 such that the pressing unit 14 extends along a line which is substantially perpendicular to the diametrical line of the emitting and receiving units 12, 13. In this embodiment, the pressing unit 14 is, but should not be limited to, a threaded rod.

When the tip portion 51 of the first digit 5 is extended into the chamber 111 confined by the ring-shaped body 11, the upper side of the tip portion 51 is subjected to the pressing action of the pressing unit 14 so as to be positioned firmly thereby. At the same time, when the infrared light emitted by the emitting unit 12 passes through a corresponding cross section of the tip portion 51, variations in blood volume due to pulsation of the heart results in varying degrees of light transmissivity so that the characteristics of infrared light received by the receiving unit 13 changes. Based upon this principle, the pulse of the tip portion 51 can be recorded by photoplethysmography to measure the pulse signal of the tip portion 51. The second measuring device 2 is used to measure a pulse signal of the toe. As the second measuring device 2 is substantially the same as the first measuring device 1 in construction and operation, a detailed description thereof is omitted herein for the sake of brevity. It is noted herein that conventional clamping type tubular digital pulse measuring devices or other suitable non-invasive types of digital pulse measuring devices can be used for implementing this invention, which is not limited to the ring-shaped measuring devices exemplified in this embodiment.

Referring back to FIG. 2, the pre-processing unit 3 includes a housing 31 in the form of a box, an analog signal processing circuit 32 and other electronic components disposed within the housing 31, and a plurality of operating keys 33 and a liquid crystal display 34 disposed on an outer surface of the housing 31. Since the measuring unit obtains the pulse signals by a non-invasive measuring method, it is difficult to distinguish physiological signals from external interference signals, particularly interference signals at 60 Hz in the environment, such as that produced by a conventional electrical power source. Moreover, as most physiological signals have a frequency ranging from 0 to 60 Hz, they have to be filtered by the analog signal processing circuit 32 of the pre-processing unit 3 to remove noise therefrom and to provide gain so as to yield accurate physiological signals.

Figure 5:
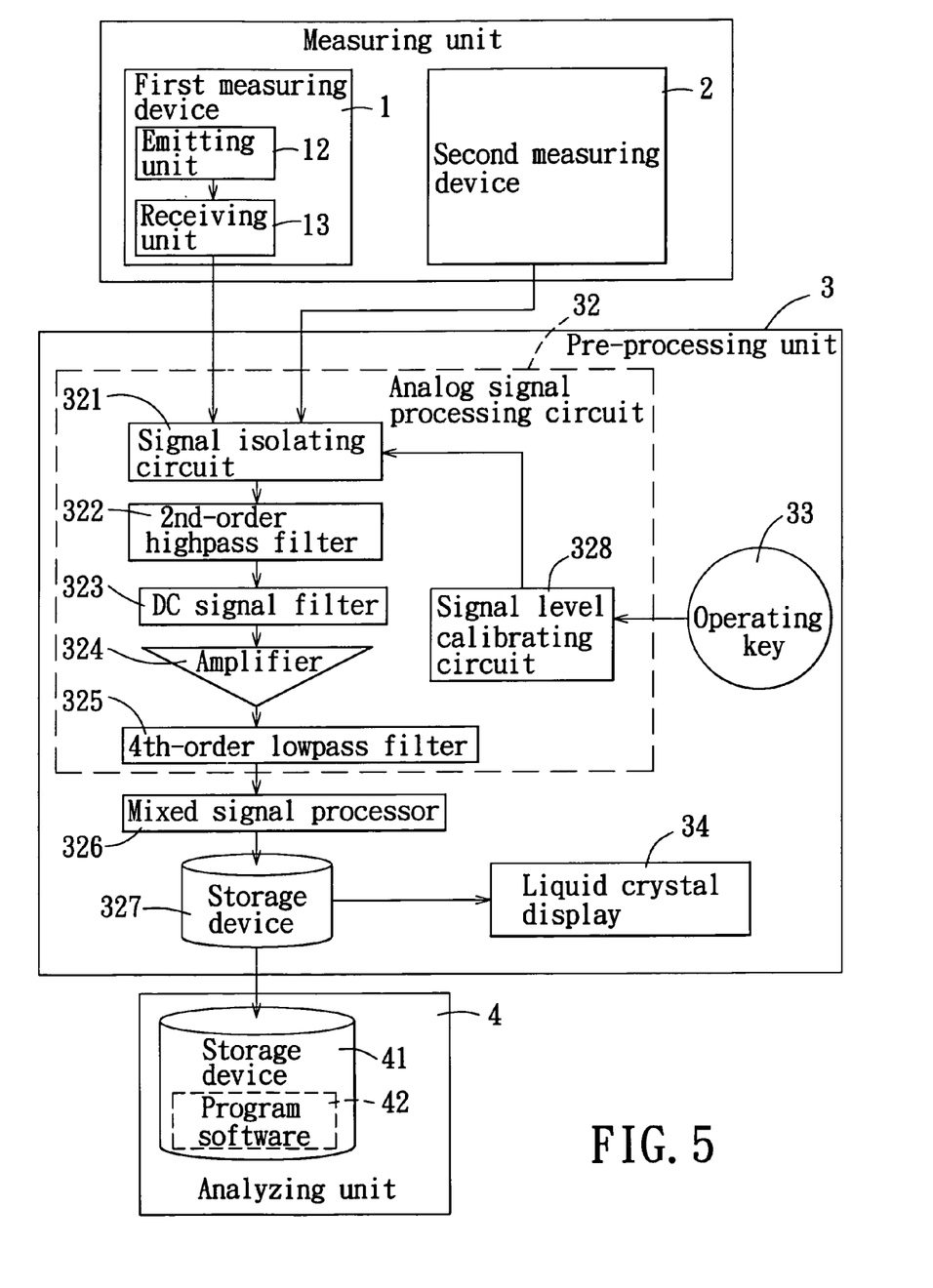
FIG. 5 is a system block diagram of the preferred embodiment.

Referring to FIGS. 2 and 5, the analog signal processing circuit 32 in this embodiment includes a signal isolating circuit 321, a second-order highpass filter 322, a direct current signal filter 323, an amplifier 324, a fourth-order lowpass filter 325, and a signal level calibrating circuit 328. The signal isolating circuit 321 is capable of distinguishing a digital pulse signal measured from the subject from a calibrated signal from the signal level calibrating circuit 328. The calibrated signal serves as a standard signal for determining the presence of a shift in the circuit parameter characteristics. Switched activation of the signal level calibrating circuit 328 can be performed through use of the operating keys 33. The direct current signal filter 323 is disposed to filter direct current signal components from the pulse signal prior to amplification thereof. It is noted that a physiological pulse signal includes direct and alternating current components, of which the alternating current signal component provides an indication of pulse changes. However, as the amplitude of the alternating current signal component is extremely small compared with that of the direct current signal component, if the direct current signal component is not removed by filtering, the alternating current signal component which is required for analysis would be very insignificant after amplification of the entire pulse signal.

The filtered signal from the direct current signal filter 323 is then amplified by the amplifier 324 to facilitate subsequent pulse analysis at the posterior end. The amplified pulse signal passes through the fourth-order lowpass filter 325 to remove 60-Hz noise interferences produced by electrical power sources and fluorescent lamps in the surrounding environment so as to yield a sufficient and reliable pulse signal. A mixed signal processor 326 includes an analog/digital converter module for analog/digital conversion of the signal from the fourth-order lowpass filter 325, and a control module for controlling operation of the pre-processing unit 3 and interaction between the measuring unit and the analyzing unit 4. The pulse signal that was digitized by the analog/digital converter module of the mixed signal processor 326 is initially stored in a storage device 327. At the same time, through a waveform display conversion algorithm stored within the storage device 327, the digitized pulse signal can be converted into a corresponding pulse waveform for display on the liquid crystal display 34. In this embodiment, the storage device 327 is a flash memory, and may be any re-writable solid-state memory device, optical storage medium (e.g., optical disk), magnetic storage device (such as magnetic disk and magnetic tape), or any other suitable digital data storage device.

In this embodiment, the analyzing unit 4 is exemplified as a personal computer linked to the pre-processing unit 3. The computer 4 has a storage device 41 which stores proprietary program software 42 executable by the computer 4. The storage device 41 may be a hard disk, an optical disk, a magnetic disk, a magnetic tape, a memory card, a flash memory, or any other suitable form of digital data storage medium. The program software 42 may be written in a suitable language, such as Microsoft Visual Basic, so as to cooperate with other software or hardware in the computer 4 to thereby configure the computer 4 for performing two major functions, namely, vasodilatation index calculation and blood flow velocity calculation (to be described hereinafter).

The invention will now be discussed in light of the vasodilatation index. Since the pulse signal of the first digit 5 (or the second digit) is recorded by measuring the transmission of infrared light through the first digit 5, the waveform thus obtained is the volume pulse of the first digit 5 caused by a change in blood volume due to pulsation of the heart. Based on the aforesaid principle, an external pressure larger than the systolic pressure of the subject is applied to the subject's wrist adjacent to the proximal end of the first digit 5 to occlude the flow of blood to the tip portion 51 of the first digit 5, and the area below the pulse waveform of the first digit 5 within a period of time after release of the external pressure is calculated. It is found that the pulse area varies with time. This indicates that the pulse area variation represents a change in the volume of blood in the blood vessel (vascular volume change) The relationship between the pulse area and the vascular blood volume can thus be quantified and expressed as a vasodilatation index (set forth hereunder), which directly reflects the degree of vasodilatation due to reactive hyperemia. The larger the index, the higher will be the degree of vasodilatation. Conversely, a smaller index indicates a lower degree of vasodilatation. The regulating function of the endothelial cells can thus be measured to serve as a basis for assessing atherosclerosis.

Index of Vasodilatation Due to Reactive Hyperemia:

$$[(\text{Comparative pulse area}-\text{standard pulse area})/\text{standard pulse area}] \times 100\% \qquad (1)$$

The analysis unit 4 stores the resultant data received thereby in the storage device 41 in an array. Since the waveform varies in magnitude and cycle beat to beat, and since each measurement entry obtained in this embodiment contains accumulated data acquired over a time interval of 5 seconds, which includes several cycles, the algorithm used in determination should be capable of determining and calculating the peaks, heart rate, pacemaker, and the area with respect to the time domain of each section of the pulse waveform. The determination of the peaks and valleys are based on a threshold value. Supposing source data received by an RS232 port or any other interface is a sequence x[n] with a length of 1000, the threshold value will be set to be:

$$\text{Threshold}=[\text{Max}(x[n])-\text{Min}(x[n])]*0.25 \qquad (2)$$

Then, each point is determined using the threshold value, as follows:

$$(\text{Max}(x[n])-x[n_1]) \leq \text{Threshold} \quad 1 \leq n_1 \leq n \qquad (3)$$

Values satisfying $n_1$ in the comparative equation are stored in the array y[n] for further determination of several largest points in y[n]. The different n values which correspond thereto are the peaks of x[n] to be found. The way to find the valleys is substantially similar to that for finding the peaks, but using a different comparative equation:

$$(x[n_1]-\text{Min}(x[n])) \leq \text{Threshold} \quad 1 \leq n_1 \leq n \qquad (4)$$

Likewise, values satisfying $n_1$ in the comparative equation (4) are stored in a scaled function array z[n] of x[n], followed by determination of several largest points of z[n]. The corresponding n values are the valleys of x[n]. After the peaks of all the cycles of the waveform have been obtained, the interval between two adjacent peaks can be used to calculate the heart rate. If the corresponding x axes of all the peaks are stored in an array Maxindex (index), the index represents the number of all the peaks in the waveform. The heart rate can be calculated using the following equation:

$$H.R. = \frac{\text{index}*1*60}{\sum_{i}^{index-1}(Maxindex(i+1)-Maxindex(i))*0.005} \qquad (5)$$

wherein 0.005 is an inverse of the sampling frequency, i.e., $\frac{1}{200}$ Hz, and also represents that the interval between two sampling points is 0.005 s. The preceding equation is used to convert the mean heart beat (interval between peaks) into frequencies multiplied by 60 to obtain the number of heart beats per minute, i.e., the so-called heart rate.

The pacemaker is determined using the peak and valley in each cycle as a range and by relying upon two time-domain characteristics: maximum amount of gradient change and maximum scaling extent after ejection. Directed to these two characteristics, the program software 42 configures the computer 4 to initially calculate the gradient changes of every 5 points between the valley and the peak (determination based on one point may not be accurate due to noise). Supposing the first five points obtained after comparison of the calculated gradients are stored in an array identified as Pacemaker, and the second comparison condition is stored in a compare (i) array:

$$\text{compare}(i)=x[\text{Pacemaker}(i)+30]-x[\text{Pacemaker}(i)] \\ 1 \leq i \leq 5 \qquad (6)$$

The maximum value in the compare (i) array is then the desired pacemaker.

Figure 6:
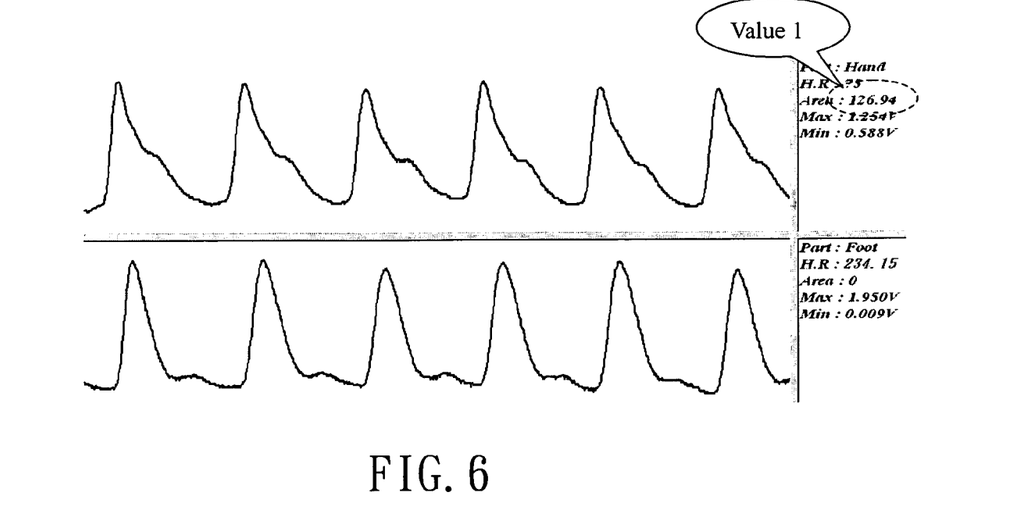
FIGS. 6 and 7 show the waveforms of pulses obtained from a 40-year-old male before and after occlusion using the preferred embodiment, and the measurement results.

In this embodiment, the standard pulse in the aforesaid equation (1) is obtained in a relaxed state wherein the subject rests in a quiet and undisturbed environment, and is allowed to lie down to relax for 10 to 15 minutes before pulse measurement. The standard pulse refers to the pulses obtained by measuring simultaneously the first digit 5 (finger) and the second digit (toe) of the subject using the first and second measuring devices 1, 2 when the subject is in the relaxed state. The measurement is the standard pulse value, and the waveforms are illustrated in FIG. 6. After obtaining the two waveforms, a pulse area algorithm of the program software 42 will enable the computer 4 to automatically integrate the pulse areas of the standard pulse and the comparative pulse in equation (1) (the pulse areas thus obtained being shown at the right side of FIG. 6). In this embodiment, the pulse area algorithm employs the known Riemann sum to do the calculation, and the sum from the pacemaker of the front segment to the valley of the rear segment, i.e., the area beneath the waveform, is calculated by using the valley of the rear segment as a baseline (to avoid miscalculation due to the effect of the baseline). Certainly, other suitable integration principles may be adopted.

After measurement of pulse in the relaxed state, an external pressure (200 mmHg in this embodiment) larger than the systolic pressure of the subject is continuously applied to the wrist of the subject for 5 minutes using a pressure cuff or strap, or other suitable constrictor means, so that oxygenated blood ejected from the ventricles cannot flow to the first digit 5. After the five-minute interval, the pressure is released, thereby entering into a comparative state in which the so-called comparative pulse in equation (1) is measured. In this embodiment, the first and second measuring devices 1, 2 measure the comparative pulses of the first digit 5 (finger) and the second digit (toe) simultaneously for a duration of 5 minutes at 30-second intervals to obtain a total of ten measurements. The measurement results and the pulse areas obtained after calculation in the same manner as described hereinabove are stored automatically in the storage device 41 of the computer 4.

Figure 7:
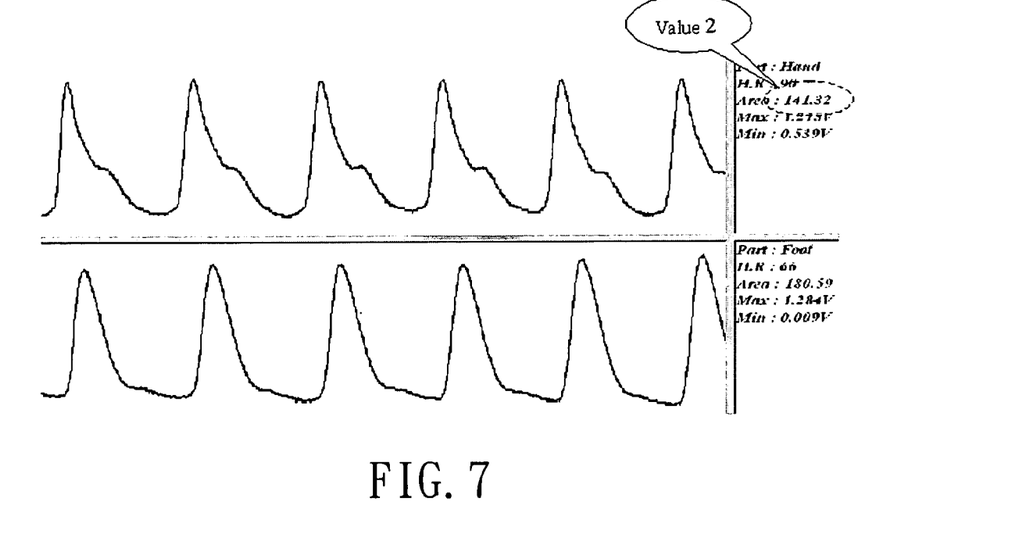

After measurement of the comparative pulses, by virtue of the program software 42, the maximal measurement value of the pulse area of each of the first digit 5 and the second digit close in time to the release of the external pressure (about 30 to 120 seconds after entry into the comparative state), i.e., the comparative pulse area in equation (1), which is exemplified as the measurement result shown in FIG. 7 for the first digit 5, is retrieved from the storage device 41. Thereafter, according to the standard pulse area and the comparative pulse area thus obtained, the index of vasodilatation due to reactive hyperemia as defined in equation (1) can be calculated.

Figure 8:
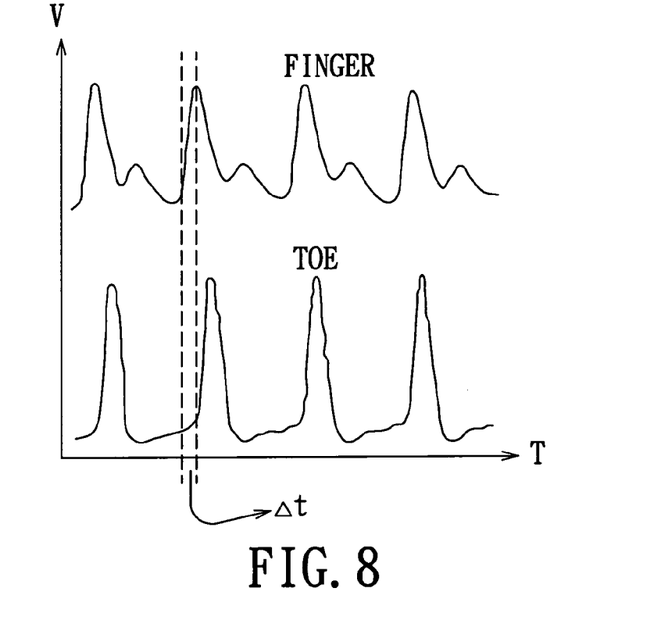
FIG. 8 is a graph illustrating the principle of obtaining the blood flow velocity defined in Equation 7 set forth hereinbelow.

Hereinafter, the calculation made by the aforesaid analyzing unit 4 in connection with the blood flow velocity will be discussed. Since the reflected wave is generated when the blood flowing to the distal vessels in the sole rebounds, in actual measurement, the reflected wave cannot be obtained by measuring the pulse of the second digit (toe). However, by using the time difference (Δt) in pacemaker between the first digit 5 (finger) and the second digit (toe) as illustrated in FIG. 8, and by dividing the time difference by the distance between the first digit 5 and the second digit as measured along the body of the subject, the flow velocity of blood during contraction of the heart can be obtained using the following equation:

Blood flow velocity=distance between the two digits/ pacemaker difference $\Delta t$     (7)

It is noted that the pacemaker can be substituted with corresponding positions on the peaks or on the pulse waveforms of the two digits.

Based on the foregoing description of the construction and functions of the components of the system according to this invention, the invention will now be explained in further detail by way of the results of measurements taken from three subjects of different physiological conditions in an experiment to prove the applicability of the system according to this invention to medical diagnoses. The first subject is a male of forty. The results of measurements obtained before and after arterial occlusion performed on the first subject are shown in FIGS. 6 and 7. The index of vasodilatation due to reactive hyperemia is:

[(141.32−126.94)/126.94]×100%=11.33%

Figure 9:
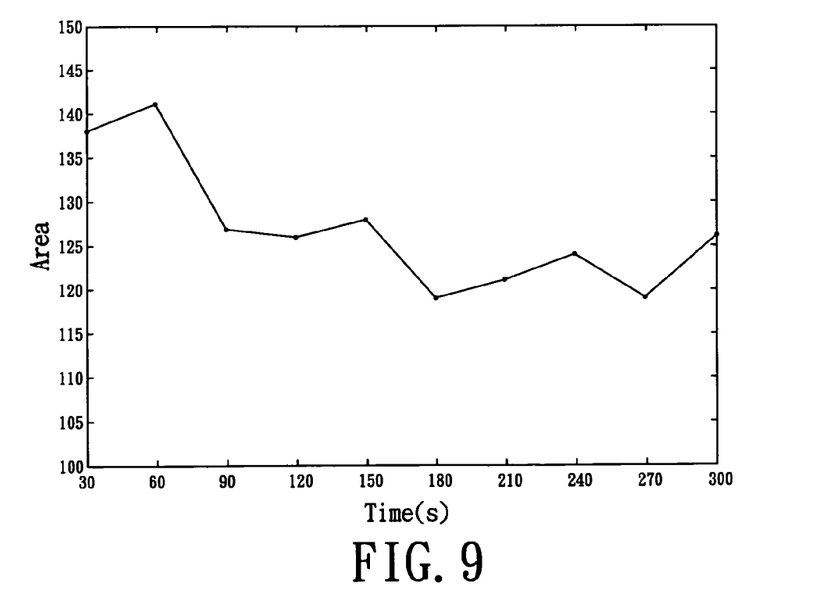
FIG. 9 is a graph illustrating the relationship between the digital pulse area and the measurement time based on the measurement results shown in FIGS. 6 and 7.

FIG. 9 illustrates the relationship between the digital pulse area (of the first digit 5) of the first subject and the measurement time. The first and second measurements taken immediately after release of the external pressure indicate that the digital pulse area increased as a result of reactive hyperemia, and that the vascular volume gradually returned to the normal state after an interval of 1.5 minutes (third measurement).

Figure 10:
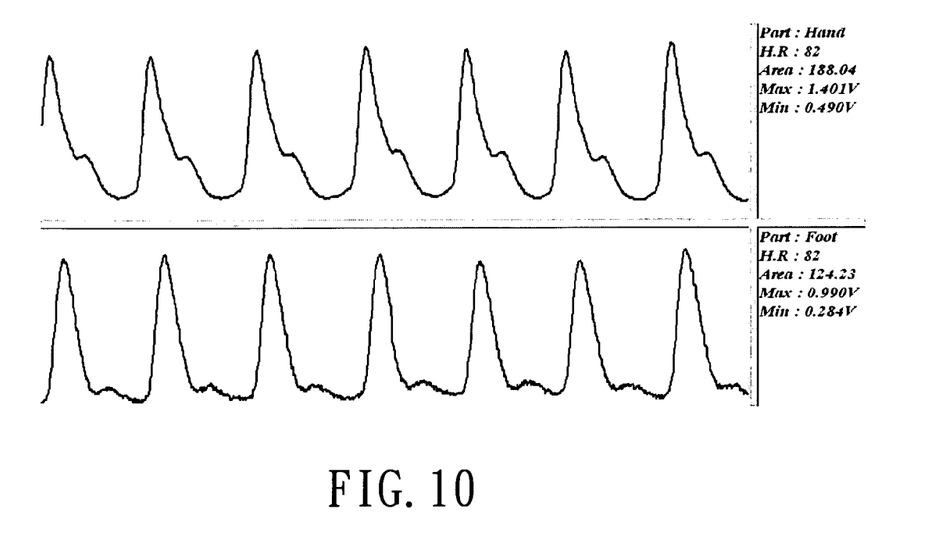
FIG. 10 is a graph showing the waveforms of pulses obtained from a 25-year-old healthy subject after occlusion using the preferred embodiment, and the measurement results.

FIG. 10 shows the reactive hyperemia measurement result obtained from the second subject, a healthy 25-year-old male, using the system of this invention. The index of vasodilatation due to reactive hyperemia is:

[(188.04−132.47)/132.47]×100%=41.95%

Figure 11:
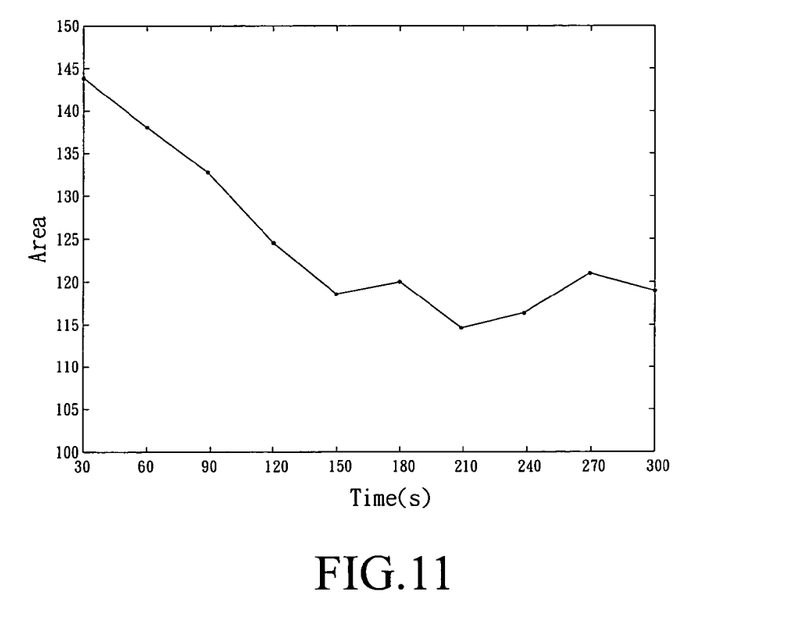
FIG. 11 is a graph illustrating the relationship between the digital pulse area and the measurement time based on the measurement result shown in FIG. 10.

FIG. 11 illustrates the relationship between the digital pulse area of the second subject and the measurement time.

Figure 12:
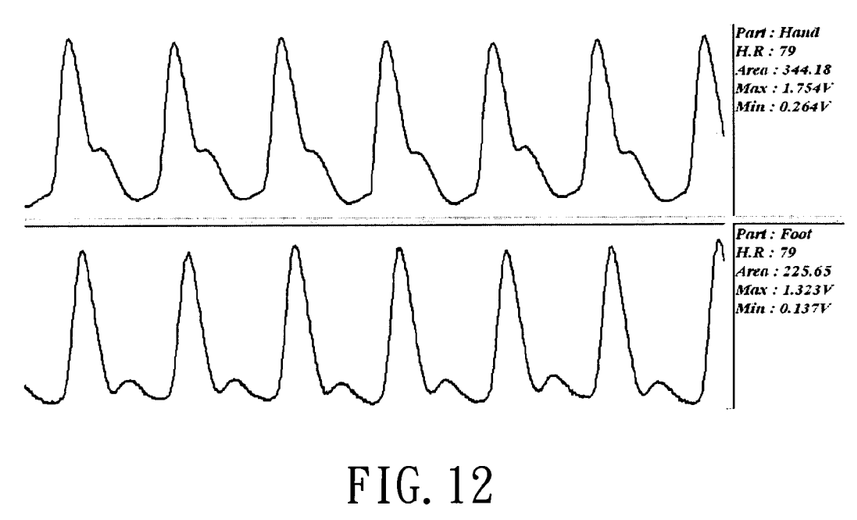
FIG. 12 shows the waveforms of pulses obtained from a 43-year-old subject with cardiovascular risk factor after occlusion using the preferred embodiment, and the measurement results.

FIG. 12 shows the reactive hyperemia measurement result obtained from the third subject, a 43-year-old male with cardiovascular risk factors, using the system of this invention. The index of vasodilatation due to reactive hyperemia is:

[(344.13−317.26)/317.26]×100%=8.46%

Figure 13:
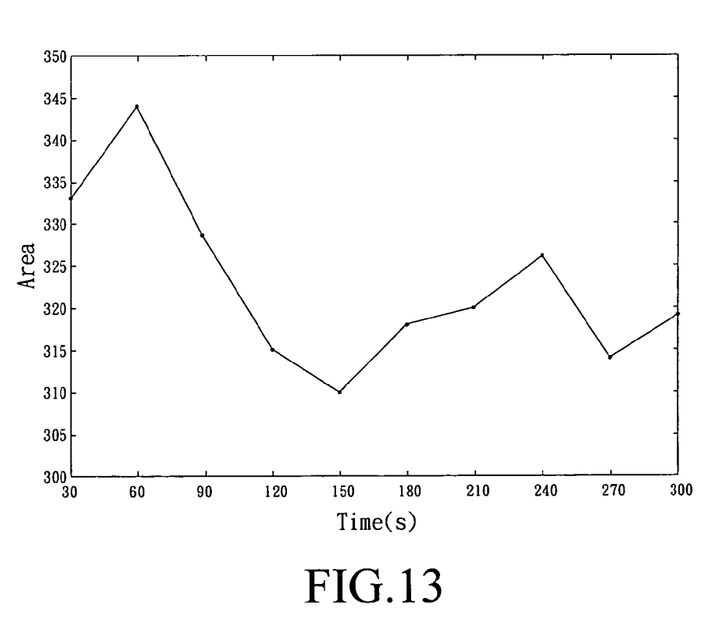
FIG. 13 is a graph illustrating the relationship between the digital pulse area and the measurement time based on the measurement result shown in FIG. 12.

FIG. 13 illustrates the relationship between the digital pulse area of the third subject and the measurement time.

Based on the aforesaid clinical tests conducted on the three subjects of different ages and physical conditions, a preliminary significant conclusion can be made, as follows:

First, in terms of the index of vasodilatation due to reactive hyperemia, the index of the second subject (male, aged 25, healthy) is the highest. Second thereto is the first subject (male, aged 40). The third subject (43-year-old male with cardiovascular risk factors) has the lowest index. It is not difficult to find that these values are inversely proportional to the age of the tested subjects, and are directly proportional to the physiological condition of the tested subjects. That is, healthier and younger subjects have a higher index, which indicates better vasodilatation and normal endothelial cell function. Conversely, the index is low in subjects of an older age or of a poor physiological condition, which is indicative of poorer vasodilatation and abnormal endothelial cell function.

Furthermore, the graphs showing the relationships between the digital pulse areas of the three subjects and the measurement times (FIGS. 9, 11 and 13) share one common attribute. That is, during the first 90 seconds after release of the external pressure, the volume of the blood vessel dilated due to reactive hyperemia, causing a rise in the waveform, and the blood vessel subsequently resumed its normal volume after 90 seconds, the waveform being gradual at that juncture. The waveforms thus obtained are consistent with the reactive hyperemia phenomenon resulting from arterial occlusion in medical studies.

It should be noted that the definition of the vasodilatation index can have other variations, and is not limited to the equation exemplified herein. Furthermore, it would be necessary to conduct further tests on a large number of subjects of different ages, sexes, and physiological conditions and to compare the test results against clinical diagnostic results in order to determine how the vasodilatation index is related to the physiological, psychiatric, or physical health conditions of the subjects and types of disease.

It is additionally noted that although the pre-processing unit 3 and the analyzing unit 4 are arranged separately, and that the latter is exemplified using a personal computer, the pre-processing unit 3 and the analyzing unit 4 may be integrated into a single electronic device. Furthermore, the signal transmission between the pre-processing unit 3 and the analyzing unit 4 may be achieved in a wired or wireless manner, or through a communications network system, such as a local area network (LAN), a wide area network (WAN), or the Internet. For instance, the measuring unit and the pre-processing unit 3 can be fixed or portable units provided at the subject end to serve as a health-monitoring home care unit, whereas the analyzing unit 4 can be provided at the physician end and linked to the pre-processing unit 3 via the Internet so that the physician can obtain in real-time the vasodilatation index and other information of the subject based on the results of the calculations made by the analyzing unit 4, and can, according to the subject's description of his/her condition or distress over the phone or the Internet, give the subject proper medical advice. As such, the subject need not visit the physician at the clinic or the hospital to obtain medical advice.

In summary, the vasodilatation index measuring and analyzing system according to this invention has the following advantages:

1. The system of this invention enables the user to measure the endothelial cell function, which is an index of atherosclerosis, in a fast and non-invasive manner so that the user can monitor his/her health conditions and take precautionary measures to prevent atherosclerosis.

2. At present, most medical instruments are of a single-channel type, i.e., they do not permit simultaneous measurement of physiological signals of the subject at different parts of the subject's body. This invention employs a multi-channel (fingers and toes) measuring system to permit cross-comparison so as to eliminate errors associated with use of a single-channel measuring system.

3. The system of this invention is simple in construction and is easy to operate. It can be used as a medical instrument for use in the home, can be carried around like a sphygmomanometer, and can be used in a medical institution such as a hospital to serve as a quantified diagnostic reference.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

We claim:

1. A vasodilatation index measuring and analyzing system, comprising:
   a constricting unit configured to apply external pressure to a limb of a subject to occlude flow of blood to a first digit of the subject;
   a measuring unit including a first measuring device configured to measure a standard pulse of the first digit of the subject, the standard pulse being measured before the application of external pressure from the constricting unit, and further configured to measure comparative pulse of the first digit of the subject, the comparative pulse being measured after release of the external pressure from the constricting unit, said standard and comparative pulses being measured for at least one cycle of application and release of said pressure;
   a pre-processing unit, coupled to said measuring unit, configured to filter noise from the standard and comparative pulse measurements obtained by the first measuring device and further configured to digitize the standard and comparative pulse measurements; and
   an analyzing unit, coupled to said pre-processing unit, wherein the analyzing unit calculates a standard and comparative pulse area of said at least one cycle of the standard and comparative pulse measurements digitized by said pre-processing unit and calculates a pre-defined index based on a difference between the standard and comparative pulse areas.

2. The vasodilatation index measuring and analyzing system according to claim 1, wherein said first measuring device measures the standard and comparative pulses of the first digit by emitting and receiving an optical signal through the first digit.

3. The vasodilatation index measuring and analyzing system according to claim 2, wherein the optical signal is infrared light.

4. The vasodilatation index measuring and analyzing system according to claim 1, wherein said analyzing unit calculates the pre-defined vasodilatation index according to the following equation:

[(comparative pulse area−standard pulse area)/standard pulse area]×100%.

5. The vasodilatation index measuring and analyzing system according to claim 1, wherein said measuring unit further includes a second measuring device configured to measure a standard pulse and a comparative pulse of a second digit of the subject simultaneously with the measuring operation of said first measuring device, said pre-processing unit filtering noise from and digitizing the standard and comparative pulses obtained by said second measuring device, a distance between the first digit and the second digit being defined as a distance measured along a body of the subject between the first digit and the second digit, corresponding positions on pulse waveforms of the first and second digits being defined as positions on the pulse waveforms respectively obtained by said first and second measuring devices at the same point of a cardiac cycle of the subject, and a time difference being defined as a difference in time between the corresponding positions, wherein said analyzing unit performs a calculation based on the following equation:

distance between the first digit and the second digit/(a time difference between corresponding positions on pulse waveforms of the first and second digits obtained respectively by said first and second measuring devices).

6. The vasodilatation index measuring and analyzing system according to claim 5, wherein the corresponding positions on the respective waveforms are pacemaker positions.

7. The vasodilatation index measuring and analyzing system according to claim 5, wherein the corresponding positions on the respective waveforms are peak positions.

8. A vasodilatation index measuring and analyzing system, comprising:
   a constricting unit configured to apply external pressure to a limb of a subject to occlude flow of blood to a first digit of the subject;
   a measuring unit including a first measuring device configured to measure a standard pulse of the first digit of the subject, the standard pulse being measured before the application of external pressure from the constricting unit, and further configured to measure a comparative pulse of the first digit of the subject after release of the external pressure from the constricting unit, said standard and comparative pulses being measured for at least one cycle of application and release of said pressure;
   a pre-processing unit, coupled to said measuring unit, configured to filter noise from the standard and comparative pulse measurements obtained by the first measuring device and further configured to digitize the standard and comparative pulse measurements; and
   an analyzing unit, coupled to said pre-processing unit, wherein the analyzing unit calculates a first pre-defined vasodilatation index based on the standard and comparative pulse measurements.

9. The vasodilatation index measuring and analyzing system according to claim 8, wherein said first measuring device measures the standard and comparative pulses of the first digit by emitting and receiving an optical signal through the first digit.

10. The vasodilatation index measuring and analyzing system according to claim 8, wherein the optical signal is infrared light.

11. The vasodilatation index measuring and analyzing system according to claim 8, wherein the analyzing unit calculates a standard and a comparative pulse area of at least one cycle of the standard and comparative pulse measurements digitized by the pre-processing unit, and wherein the first pre-defined vasodilatation index is based on a difference between the standard and the comparative pulse areas.

12. The vasodilatation index measuring and analyzing system according to claim 11, wherein the first pre-defined vasodilatation index is calculated according to the following formula:

[(comparative pulse area standard pulse area)/standard pulse area]×100%.

13. The vasodilatation index measuring and analyzing system according to claim 8, wherein the measuring unit further includes a second measuring device configured to measure a standard pulse and a comparative pulse of a second digit of the subject simultaneously with the measuring operation of the first measuring device, and wherein said pre-processing unit further filters noise from and digitizes the standard and comparative pulses obtained by said second measuring device, a distance between the first digit and the second digit being measured along a body of the subject between the first digit and the second digit, corresponding positions on a first pulse waveform of the first digit and a second pulse waveform of the second digit being positions on the pulse waveforms respectively obtained by said first and second measuring devices at a same point of a cardiac cycle of the subject, and a time difference being a difference in time between the corresponding positions on the first and second pulse waveforms, wherein the analyzing unit calculates a second pre-defined vasodilatation index based on the following formula:

> distance between the first digit and the second digit/(a time difference between corresponding positions on pulse waveforms of the first and second digits obtained respectively by said first and second measuring devices).

14. The vasodilatation index measuring and analyzing system according to claim 13, wherein the corresponding positions on the first and the second pulse waveforms are pacemaker positions.

15. The vasodilatation index measuring and analyzing system according to claim 13, wherein the corresponding positions on the first and the second pulse waveforms are peak positions.

* * * * *